(12) United States Patent
Brenizer et al.

(10) Patent No.: US 10,953,197 B2
(45) Date of Patent: Mar. 23, 2021

(54) GUIDE EXTENSION CATHETER

(71) Applicant: Teleflex Life Sciences Limited, Valletta (MT)

(72) Inventors: Joshua Brenizer, Oak Grove, MN (US); Dean Peterson, Minneapolis, MN (US); Thomas Kouchoukos, Edina, MN (US); Mark Wendle, Albany, NY (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

(21) Appl. No.: 16/644,365

(22) PCT Filed: Oct. 30, 2019

(86) PCT No.: PCT/US2019/058794
§ 371 (c)(1),
(2) Date: Mar. 4, 2020

(87) PCT Pub. No.: WO2020/146035
PCT Pub. Date: Jul. 16, 2020

(65) Prior Publication Data
US 2021/0008343 A1    Jan. 14, 2021

Related U.S. Application Data

(60) Provisional application No. 62/789,000, filed on Jan. 7, 2019.

(51) Int. Cl.
*A61M 25/01* (2006.01)
*A61M 39/06* (2006.01)
*A61M 25/00* (2006.01)

(52) U.S. Cl.
CPC .... *A61M 25/0138* (2013.01); *A61M 25/0102* (2013.01); *A61M 39/06* (2013.01);
(Continued)

(58) Field of Classification Search
CPC ............. A61M 25/0138; A61M 39/06; A61M 25/0102; A61M 2025/0047; A61M 2210/125
See application file for complete search history.

(56) References Cited

U.S. PATENT DOCUMENTS

| 4,000,739 A | 1/1977 | Stevens |
| 4,289,128 A | 9/1981 | Rusch |

(Continued)

FOREIGN PATENT DOCUMENTS

| CA | 2008784 C | 7/2002 |
| DE | 69928825 | 7/2006 |

(Continued)

OTHER PUBLICATIONS

Bertrand, Michel E. "The Evolution of Cardiac Catheterization and Interventional Cardiology," European Society of Cardiology, 2006, 10 pages.

(Continued)

*Primary Examiner* — Amber R Stiles
(74) *Attorney, Agent, or Firm* — Robert B. Madden; Gregory W. Smock

(57) ABSTRACT

Guide extension catheters and related methods are disclosed. A guide extension catheter can comprise an elongate tube member, a push member, and a removable support member. The push member can be eccentrically coupled directly or indirectly to the elongate tube member and can extend proximally therefrom for slidably positioning the elongate tube member within and partially beyond a distal end of a guide catheter. The removable support member can comprise a structure that surrounds at least a portion of the push member. The removable support member alone, or when placed over the push member, can be more rigid along its longitudinal axis than the elongate tube member and can (Continued)

have a cross-sectional dimension that is greater than a maximal cross-sectional dimension of the push member.

20 Claims, 9 Drawing Sheets

(52) U.S. Cl.
CPC ............... *A61M 2025/0047* (2013.01); *A61M 2210/125* (2013.01)

(56) References Cited

U.S. PATENT DOCUMENTS

| | | | |
|---|---|---|---|
| 4,723,936 A | 2/1988 | Buchbinder et al. |
| 4,762,129 A | 8/1988 | Bonzel |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Yock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,350,395 A | 9/1994 | Yock |
| 5,368,567 A | 11/1994 | Lee |
| 5,383,853 A | 1/1995 | Jung et al. |
| 5,413,560 A | 5/1995 | Solar |
| 5,415,639 A | 5/1995 | VandenEinde et al. |
| 5,439,445 A | 8/1995 | Kontos |
| 5,439,447 A | 8/1995 | Miraki |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,292,850 B2 | 10/2012 | Root et al. |
| 8,814,890 B2 | 8/2014 | Miyata et al. |
| RE45,380 E | 2/2015 | Root et al. |
| 8,996,095 B2 | 3/2015 | Anderson et al. |
| 9,144,662 B2 | 9/2015 | Caprio et al. |
| RE45,760 E | 10/2015 | Root et al. |
| RE45,776 E | 10/2015 | Root et al. |
| 9,352,123 B2 | 5/2016 | Zhou et al. |
| RE46,116 E | 8/2016 | Root et al. |
| 9,486,611 B2 | 11/2016 | Petersen et al. |
| 9,993,613 B2 | 6/2018 | Wang et al. |
| 10,173,029 B2 | 1/2019 | Webster et al. |
| RE47,379 E | 5/2019 | Root et al. |
| 10,751,514 B2 | 8/2020 | Brenizer et al. |
| 2001/0016712 A1 | 8/2001 | Hamilton |
| 2002/0165598 A1* | 11/2002 | Wahr ............... A61B 17/12045 623/1.11 |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0127927 A1 | 7/2004 | Adams |
| 2004/0236215 A1 | 11/2004 | Mihara et al. |
| 2005/0004523 A1 | 1/2005 | Osborne et al. |
| 2005/0015073 A1 | 1/2005 | Kataishi et al. |
| 2005/0182437 A1 | 8/2005 | Bonnette et al. |
| 2006/0247661 A1 | 11/2006 | Richards et al. |
| 2007/0260219 A1 | 11/2007 | Root et al. |

(56) References Cited

U.S. PATENT DOCUMENTS

| | | |
|---|---|---|
| 2008/0243171 A1 | 10/2008 | Ressemann et al. |
| 2009/0005755 A1 | 1/2009 | Keith et al. |
| 2009/0264865 A1 | 10/2009 | Kawai |
| 2013/0072904 A1 | 3/2013 | Musbach et al. |
| 2013/0116701 A1* | 5/2013 | Wang .................. A61M 25/01 606/108 |
| 2013/0197483 A1 | 8/2013 | Anderson et al. |
| 2014/0018773 A1 | 1/2014 | Wang et al. |
| 2014/0039461 A1 | 2/2014 | Anderson et al. |
| 2014/0081243 A1 | 3/2014 | Zhou et al. |
| 2014/0142506 A1 | 5/2014 | Prindle et al. |
| 2014/0276618 A1 | 9/2014 | Di Caprio et al. |
| 2015/0151090 A1 | 6/2015 | Sutton et al. |
| 2016/0346515 A1 | 12/2016 | Buller et al. |
| 2018/0161547 A1 | 6/2018 | Brenizer et al. |
| 2019/0366049 A1* | 12/2019 | Hannon ............ A61M 25/0662 |
| 2020/0338317 A1 | 10/2020 | Brenizer et al. |
| 2021/0008342 A1 | 1/2021 | Buller et al. |
| 2021/0008355 A1 | 1/2021 | Peterson et al. |

FOREIGN PATENT DOCUMENTS

| | | |
|---|---|---|
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 0992260 B1 | 9/2007 |
| JP | 2004275435 A | 10/2004 |
| WO | 1984003633 A1 | 9/1984 |
| WO | 1997037713 A1 | 10/1997 |
| WO | 2000024451 A9 | 11/2000 |
| WO | 2016191415 A1 | 12/2016 |
| WO | 2017019900 A1 | 2/2017 |

OTHER PUBLICATIONS

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

Iqbal et al. "Coronary stents: historical development, current status and future directions," British Medical Bulletin, 2013, 106: 193-211.

PCT International Search Report and Written Opinion dated Jan. 10, 2020 in PCT Application No. PCT/US2019/058794.

Takahashi, Saeko. "New Method to Increase a Backup Support of a 6 French Guiding Coronary Catheter," Catheterization and Cardiovascular Interventions 63:452-456 (2004), 5 pages, published online in Wiley InterScience (www.interscience.wiley.com).

Topol, Eric J. "Textbook of Interventional Cardiology," Saunders Elseveir, 5th Edition, 2008, p. 277-280.

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet.

Vascular Solutions, Inc. "GuideLiner V3 catheter: Guide Extension Catheter with Half-Pipe Technology" [Brochure], Dec. 2013, Minneapolis, MN.

* cited by examiner

GUIDE EXTENSION CATHETER

CLAIM OF PRIORITY

This application is a national stage application under 35 U.S.C. § 371 of PCT application no. PCT/US2019/058794, filed Oct. 30, 2019, which claims priority to U.S. provisional patent application No. 62/789,000, entitled "GUIDE EXTENSION CATHETER" and filed on Jan. 7, 2019, both of which are herein incorporated by reference in their entirety.

TECHNICAL FIELD

The subject matter of this patent document relates to the field of medical devices. More particularly, but not by way of limitation, the subject matter relates to guide extension catheters for use with guide catheters.

BACKGROUND

Interventional cardiology procedures often involve inserting guidewires or other instruments through catheters into coronary arteries that branch off from the aorta. In coronary artery disease, a coronary artery may be narrowed or occluded by atherosclerotic plaques or other lesions. These lesions may totally obstruct the lumen of the artery or may dramatically narrow the lumen of the artery. Narrowing is referred to as stenosis. In order to diagnose and treat obstructive coronary artery disease, it is commonly necessary to pass a guidewire or other instruments through and beyond the occlusion or stenosis of the coronary artery.

To treat a stenosis, a guide catheter can be inserted through the aorta and into the ostium of the coronary artery. This is sometimes accomplished with the aid of a guidewire. The guide catheter is typically seated into the opening or ostium of the artery to be treated and a guidewire or other instrument is passed through the lumen of the guide catheter and inserted into the artery beyond the occlusion or stenosis. Crossing tough lesions or tortuous anatomy can create enough backward force to dislodge the guide catheter from the ostium of the artery being treated. This can make it difficult or impossible for the interventional cardiologist to treat certain forms of coronary artery disease.

A coaxial guide catheter can be used in conjunction with a standard guide catheter to provide additional backup support. The coaxial guide catheter can be passed through the standard guide catheter until its distal end extends beyond the distal end of the standard guide catheter, thereby positioning the distal end of the coaxial guide catheter further within the branch artery harboring the stenosis. Coaxial guide catheters may thus be referred to as guide extension catheters.

OVERVIEW

The present inventors recognize that there is a need to provide guide extension catheters that are compatible with guide catheters for performing interventional procedures in challenging anatomy, e.g., narrow blood vessels harboring robust occlusions. The present inventors also recognize that there is a need to provide increased push strength and distal maneuverability to guide extension catheters during interventional procedures without sacrificing the cross-sectional area of the guide extension catheter available for interventional device delivery and afforded backup support. A guide extension catheter that includes a push member surrounded, at least in part, by a removable support member can be used in conjunction with a guide catheter to access discrete regions of coronary or peripheral vasculature and to facilitate accurate placement of interventional devices without guide catheter back-out from a vessel ostium or branch of interest. The guide extension catheter can further include a distal hydrophilic coating to reduce friction, thereby enhancing deliverability of the catheter while minimizing loss of backup support.

Guide extension catheters and related methods are disclosed in this patent document. A guide extension catheter can comprise an elongate tube member (also referred to as a tube member or guide extension tubing), push member (also referred to as a substantially rigid portion, push rod, or push wire), and a removable support member positioned around the push member, proximal to the elongate tube member. The push member, which may comprise a narrow or small-diameter wire, can be eccentrically coupled to the tube member for slidably positioning the tube member within and partially beyond a distal end of a guide catheter and a vessel ostium of interest, a process aided by the removable support member.

These and other embodiments and features of the present guide extension catheters and related methods will be set forth, at least in part, in the following Detailed Description. This Overview is intended to provide non-limiting embodiments of the present subject matter; it is not intended to provide an exclusive or exhaustive explanation of the disclosed embodiments. The Detailed Description below is included to provide further information about the present guide extension catheters and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

This patent document discloses guide extension catheters to be placed within guide catheters for providing support and guidance in a vessel when percutaneously advancing interventional devices, such as guidewires, balloon catheters, stents, or stent catheters. A guide extension catheter is configured to be passed through a main lumen of a guide catheter so that its distal end portion can be extended beyond a distal end of the guide catheter and into the desired vessel while its intermediate portions remain within the guide catheter, for example as described in U.S. Pat. Nos. 8,048,032, 8,142,413, RE45,760, RE 45,380, RE45,776, and RE46,116, which are incorporated by reference in their entireties herein. The guide extension catheter may have enhanced push strength, via a removable support member surrounding a push member, without reducing the cross-sectional space available for passage of interventional devices therethrough. The guide extension catheter may include a hydrophilic coating on a distal portion thereof to improve deliverability without reducing backup support.

It is believed that the present guide extension catheters will find great utility by interventional cardiologists performing percutaneous transluminal coronary interventions. Although the remainder of this patent document generally discusses and illustrates such uses, it should be understood that the guide extension catheters can also be used for treating other non-coronary diseased vessels or other hollow structures (e.g., biliary tract, ureter, etc.) throughout a patient's body where interventional devices are or can be employed.

Figure 1:
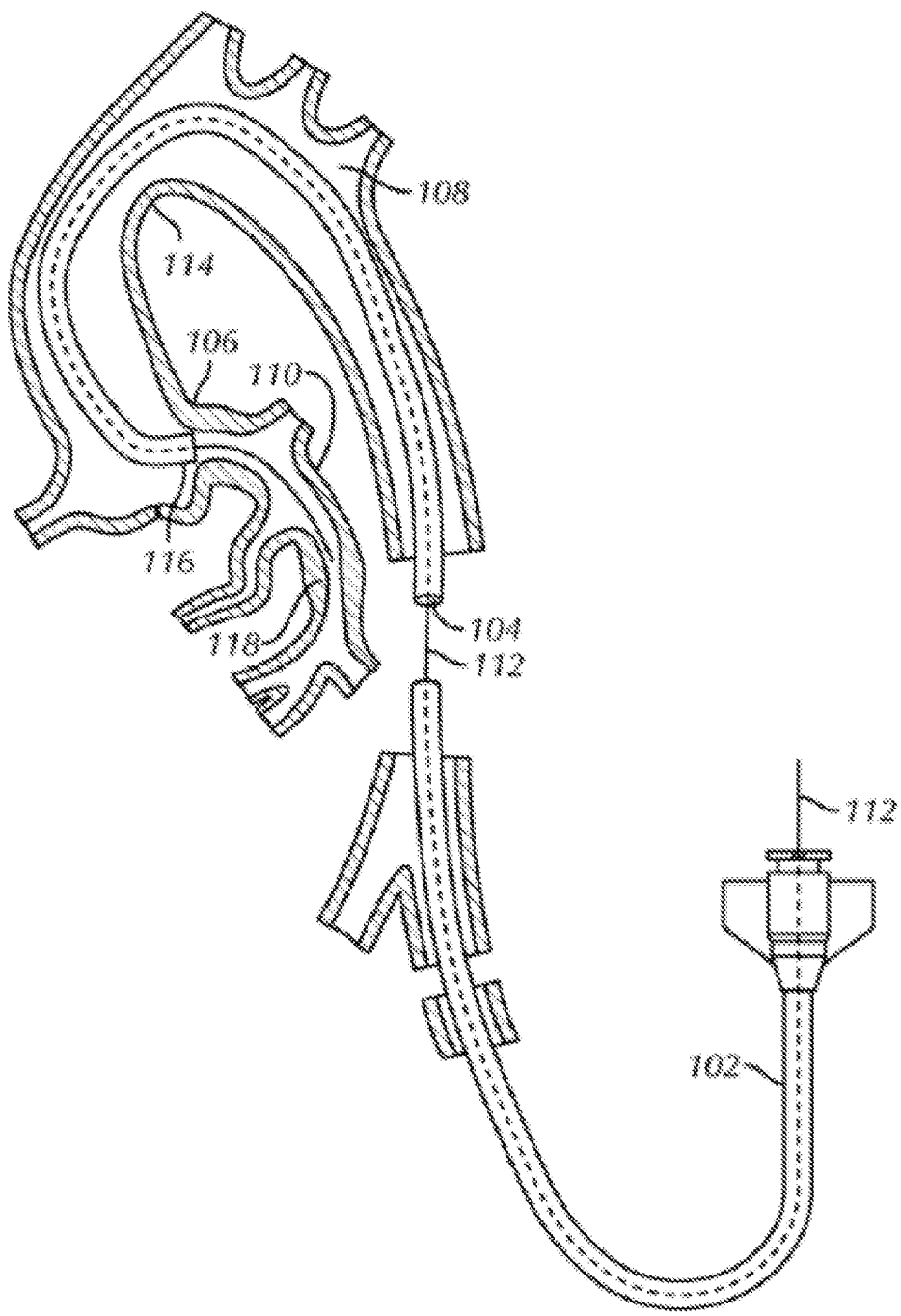
FIG. 1 illustrates a plan view of a guide catheter advanced through an aorta to an ostium of a coronary vessel.

Minimally invasive cardiac interventions are utilized throughout the world and often include the use of a guidewire 112 and a guide catheter 102, as illustrated in FIG. 1. The guidewire 112 can comprise an elongate, small-diameter member designed to navigate vessels to reach a diseased site or vessel segment of interest. Guidewires can come in various configurations, including solid steel or nitinol core wires and/or solid core wire wrapped in a smaller wire coil or braid, for example. The guide catheter 102 can comprise an elongate tube member defining a main lumen 104 along its length. The guide catheter 102 can be formed of polyurethane, for example, and can be shaped along its distal portion to facilitate advancement to a coronary ostium 106 (or other region of interest within a patient's body). Any sized guide catheter 102, such as a 6 F, 7 F, or 8 F guide catheter, where F is an abbreviation for the French catheter scale (a unit to measure catheter diameter (1 F=⅓ mm)), can be inserted at a femoral or radial artery and advanced through an aorta 108 to a position adjacent to the ostium 106 of a coronary artery 110.

In a typical procedure, the guidewire 112 (or a shorter, thicker introducer guidewire) and guide catheter 102 can be advanced through the arch 114 of the aorta 108 to the ostium 106. The guidewire 112 may then be advanced beyond the ostium 106 and into the coronary artery 110. The diameter and rigidity of the guide catheter's distal end 116, however, may not permit the device to be advanced beyond the ostium 106 and into the coronary artery 110.

Maintaining the position of the guide catheter's distal end 116 at the ostium 106 can facilitate the guidewire 112 or other interventional device successfully reaching the diseased site (e.g., a stenotic lesion 118) through its further distal advancement. With the guide catheter 102 in position, force can be applied to the guidewire's proximal end to push the guidewire 112 to and beyond the lesion 118, and a treating catheter (optionally including a balloon or stent) can be passed over the guidewire 112 to treat the site. The application of force to the guidewire 112 or the treating catheter can sometimes cause the guide catheter 102 to dislodge from the ostium 106 of the coronary artery 110, and, in such instances, the guidewire or treating catheter must be further distally advanced independently of the guide catheter's alignment and support to reach the lesion 118. This can occur in the case of a tough stenotic lesion 118 or tortuous anatomy, where it is often difficult to pass the guidewire 112 or the treating catheter to and beyond the lesion. A heart's intrinsic beat can also cause the guide catheter's distal end 116 to lose its positioning or otherwise be shifted so that it no longer is positioned to align and support the guidewire 112 or the treating catheter into the portion of the coronary artery 110 including the lesion 118.

Figure 2:
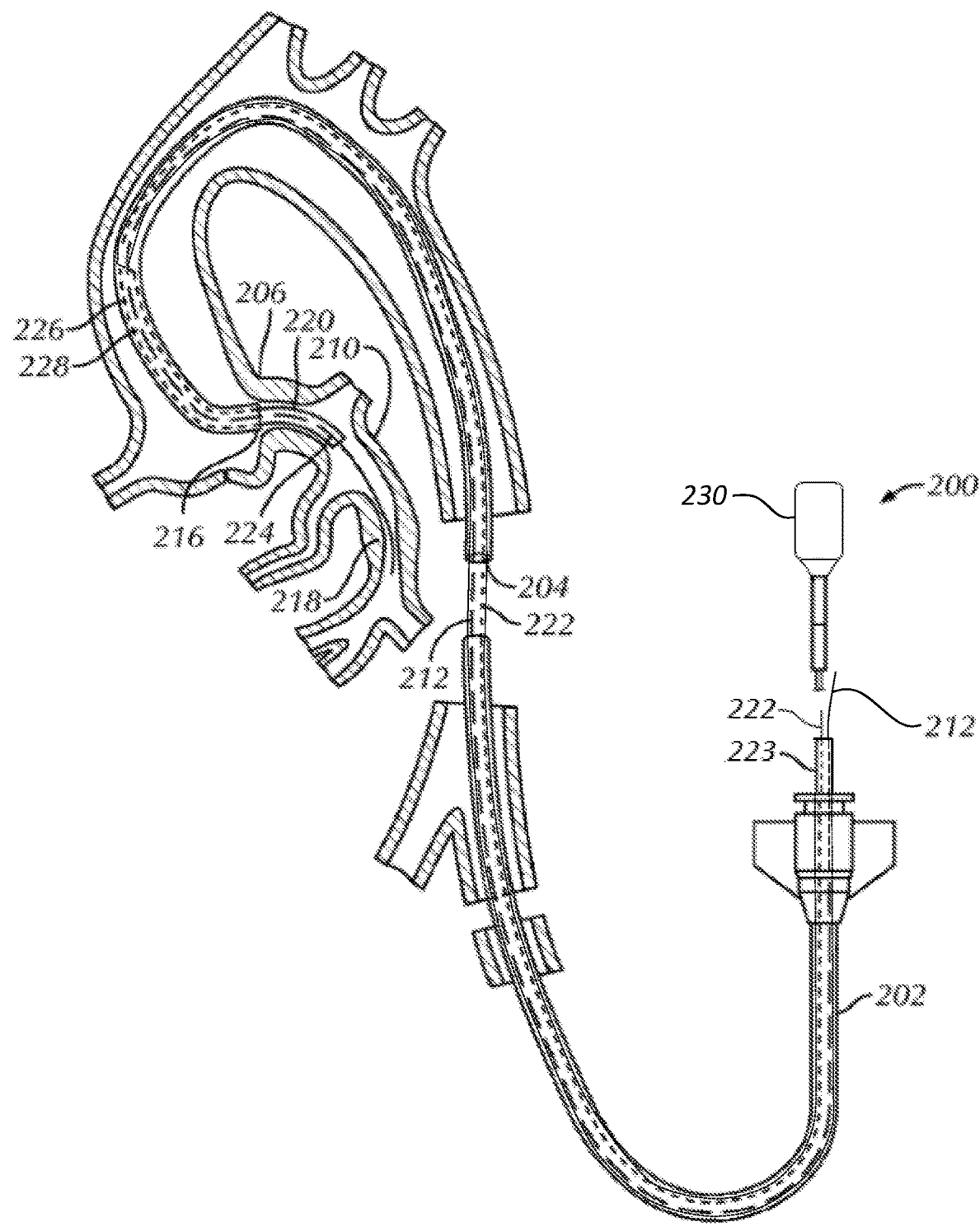
FIG. 2 illustrates a plan view of a guide extension catheter, as constructed in accordance with at least one embodiment, used in conjunction with a guide catheter for the delivery of an interventional device into an occluded vessel for treatment.

As illustrated in FIG. 2, the present guide extension catheter 200 can improve access to a coronary artery 210 and a stenotic lesion 218. The guide extension catheter 200 can include a relatively flexible elongate tube member 220 and a push member 222 having a collective length that is greater than a length of a guide catheter 202 (e.g., 130 cm-175 cm, or greater). An outer diameter of the tube member 220 can be sized to permit insertion of its distal end portion 224 into a coronary artery or its branches containing the lesion 218, thereby providing alignment and support for an interventional device (e.g., a treating catheter) beyond the distal end 216 of the guide catheter 202 to the lesion and beyond. The extension of the tube member 220 into a smaller-sized artery or branch also serves to maintain the position of the guide catheter 202 at an artery's ostium 206 during an operation. The push member 222, which may comprise a solid steel or nitinol core wire and/or solid core wire wrapped in a smaller wire coil or braid, can be at least temporarily surrounded by a removable support member 223, which may comprise an elongate tube, e.g., hypotube, configured to provide additional push strength during insertion of the guide extension catheter 200 within the coronary artery 210. The length of the removable support member 223 may be approximately equal to, or slightly less than, the length of the push member 222.

The operating physician can advance the distal end portion 224 of the tube member 220 over a guidewire 212 and through and beyond the guide catheter's distal end 216 into the coronary artery 210 by applying a longitudinal force to the removable support member 223 and optionally the push member 222. A proximal end portion 226 of the tube member 220 can remain within the guide catheter 202. The operating physician may then retract the removable support member 223 from the patient, such as by sliding it proximally over the push member 222, thereby creating additional space within the coronary artery 210 for insertion of one or more interventional treatment devices. The physician can subsequently deliver a treating catheter over the guidewire 212, through a main lumen 204 of the guide catheter 202, and through a lumen 228 of the tube member 220 until the working portion of the treating catheter is located beyond the distal end portion 224 of the tube member. The operating physician can then treat the lesion 218 using standard techniques with added backup support on the guide catheter 202, thereby providing an extra ability to push and advance the treating catheter.

In general, the lumen 228, and hence the tube member 220, can be sized and shaped to pass one or more interventional devices such as the guidewire and the treating catheter therethrough. The cross-sectional shape of the lumen 228 can be similar to the cross-sectional shape of the guide catheter's main lumen 204. For instance, in some examples, the cross-sectional shape of the lumen 228 can be generally uniform along its length. In other examples, the cross-sectional diameter may vary along the length of the tube member 220. According to embodiments of such examples, the distal end portion 224 of the tube member 220 may be more narrow, e.g., tapered, relative to the proximal end portion 226, for instance. In addition or alternatively, the proximal and distal portions of the tube member 220 can be separated by one or more tapered portions. The length of each differently-sized portion of the tube member 220 in such embodiments can also vary, and in some examples, the distal portion 224 of the tube member can be the longest. In examples that include differently sized proximal and distal portions, the difference in diameter between the proximal portion 226 and the distal portion 224 of the tube member may be from about 1F to about 4F, or anywhere in between.

The outer diameter of the tube member 220 can assume maximum cross-sectional dimensions that allow the tube member 220 to coaxially slide into and through the guide catheter 202. In other embodiments, the outer cross-sectional dimensions of the tube member 220 can be less than the allowable maximum. For example, in an 8 F guide catheter, the tube member 220 can have about a 7 F, 6 F, 5 F, 4 F or lesser diameter, or any diameter therebetween. In some embodiments, a diameter of the lumen 228 of the tube member 220 is not more than about one French size smaller than a diameter of the lumen 204 of the guide catheter 202. In one embodiment, the guide extension catheter 200 can be made in at least three sizes corresponding to the internal capacity of 8 F, 7 F, and 6 F guide catheters that are commonly used in interventional cardiology procedures. The difference in size between the outer diameter of the tube member 220 and the inner diameter of the guide catheter 202 may vary. For instance, the gap in cross-sectional diameter between the inner diameter of the guide catheter and the outer diameter of the tube member 220 may be less than and/or about 0.001 in., 0.002 in., 0.003 in., 0.004 in., or 0.005 in., or any distance therebetween. In specific embodiments, the cross-sectional diameter gap may range from about 0.002 to 0.003 in., or about 0.002 to 0.0035 in. For example, where a guide catheter has an inside diameter of 0.070 in. and the guide extension catheter has an outside diameter of 0.068 in., the gap would be 0.002 in. The diameter gap between an outer diameter of the tube member 220 and the lumen 204 of the guide catheter 202 may also be generally continuous along a substantial portion of the length or a majority of the length of the tube member 220 in some embodiments, or the diameter gap may increase along one or more distal portions of the tube member 220. In various embodiments, a tube member 220 with any diameter may be used. The length of the tube member 220 can be substantially less than the length of the guide catheter 202; however, the tube member 220 can be designed with any length according to a desired application, such as about 6 to about 45 cm, about 10 to about 35 cm, about 14 to about 25 cm, or about 18 to about 20 cm.

The push member 222 can be attached to the proximal end portion 226 of the tube member 220 and can extend proximally from this attachment to a handle member 230 (also referred to as a manipulation member) accessible to an operating physician outside of a patient's body. The removable support member 223 can be coupled, at its most proximal end, with the handle member 230, such that movement of the handle member 230 causes movement of the removable support member 223. The handle member 230, push member 222 and removable support member 223 can allow the physician to position the tube member 220 between a first position, entirely within the guide catheter 202, and the illustrated second position, in which the tube member's distal end 224 extends beyond that of the guide catheter 202 and into the coronary artery 210. Together, the push member 222 and removable support member 223 can be rigid enough to allow the guide extension catheter 200 to be inserted through the guide catheter 202 upon receiving a pushing force from a physician via the handle member 230. The distal end of the removable support member 223 may be free, i.e., not coupled or attached, to the tube member 220, but may contact a proximal end of the tube member 220 in response to a manual push force. In some examples, the push member 222 can be more rigid along its longitudinal axis than the tube member 220, and may generally comprise a wire or narrow rod. The removable support member 223 can comprise a tubular structure that is also more rigid along its longitudinal axis than the tube member 220. In specific embodiments, the removable support member 223 may comprise a stainless steel tube.

Figure 3:
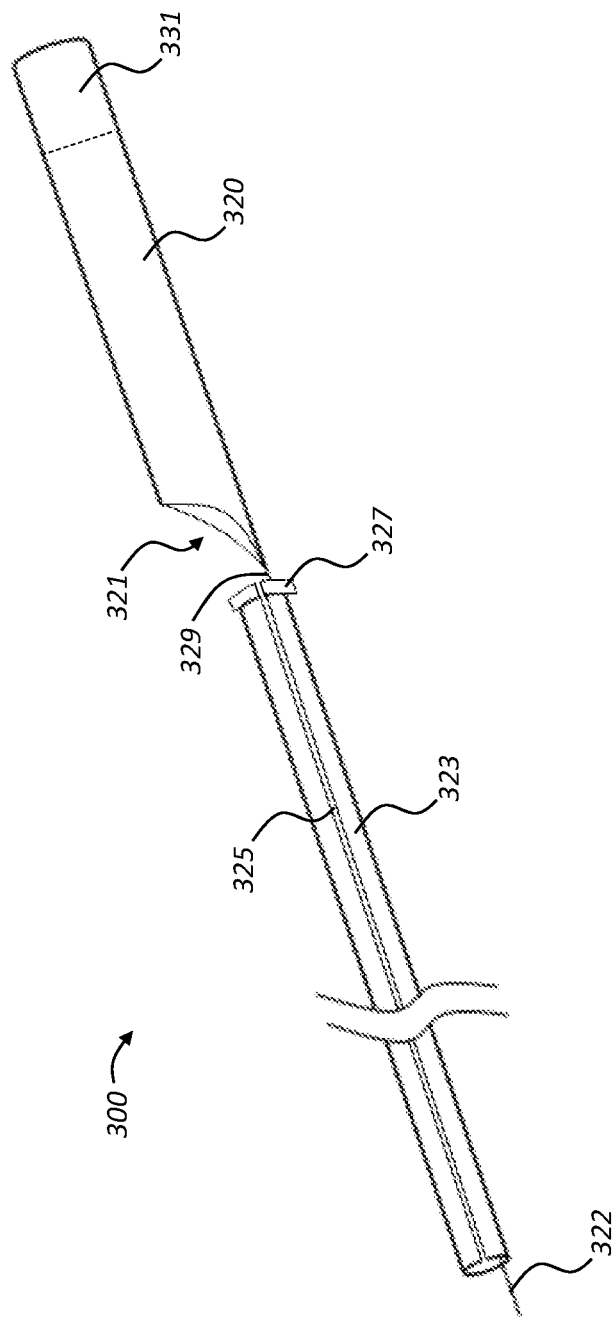
FIG. 3 illustrates a perspective view of a guide extension catheter, as constructed in accordance with at least one embodiment, showing a removable support member surrounding a push member.

FIG. 3 illustrates a perspective view of an example guide extension catheter 300 in accordance with embodiments of the present disclosure. As shown, the guide extension catheter 300 can include an elongate tube member 320 coupled with a push member 322 at the push member's distal end 329. Surrounding the push member 322 is a removable support member 323, which may include a longitudinal slit 325 that extends along its length. The slit 325 can be formed to be resiliently closed, such that it can be forcibly peeled open to remove the removable support member 323 from the push member 322. A distal end of the removable support member 323 may include a stop or lip member 327 configured to prevent the removable support member 323 from damaging the elongate tube member 320 near or at its proximal opening 321. The lip member 327 may generally comprise a substantially soft, elastic or otherwise depressible material configured to impact the elongate tube member 320 without damaging it during insertion of the guide extension catheter 300 into a vessel.

A distal portion 331 of the elongate tube member 320 can be coated with a friction-reducing material, e.g., a hydrophilic material, to improve the maneuverability of the elongate tube member's leading, i.e., distal, end, which may be the first end to encounter sinuous vasculature. Coating only or primarily the distal portion 331 may improve deliverability of the guide extension catheter 300 without sacrificing backup support. The length of the distal portion 331 covered by the friction-reducing material may vary, for example extending proximally from the most distal tip of the elongate tube member 320 for about 5 cm or less, about 10 cm, about 15 cm, about 20 cm, about 25 cm, or about 30 cm or more, or any length therebetween.

The push member 322 may comprise a rod or wire, such as a circular wire having a cross-sectional diameter of about 0.014 inches or less, or a diameter ranging from less than 0.010 to about 0.010, 0.012, 0.014, 0.016, 0.018, 0.020, 0.022, 0.024 inches or more, or any diameter therebetween.

Due to the optionally narrow diameter of the push member 322, the removable support member 323 may provide the structural support necessary to urge the tube member 320, and thus the entire guide extension catheter 300, through one or more vessels. After full insertion of the guide extension catheter 300, such that the distal end of the elongate tube 320 reaches a target site, the removable support member 323 can be removed by sliding it proximally along the push member 322. In some examples, the removable support member 323 can be opened via the slit 325 during and/or after its removal from the vasculature to allow removal of the push member 322 therefrom. Embodiments may involve urging the push member 322 through the slit 325 before, during and/or after sliding the removable support member 323 proximally away from a target site. After removal of the removable support member 323, the narrow cross-sectional diameter of the remaining push member 322 may allow one or multiple interventional devices to be inserted through the elongate tube member 320 with minimal interference from the push member 322.

Figure 4A:
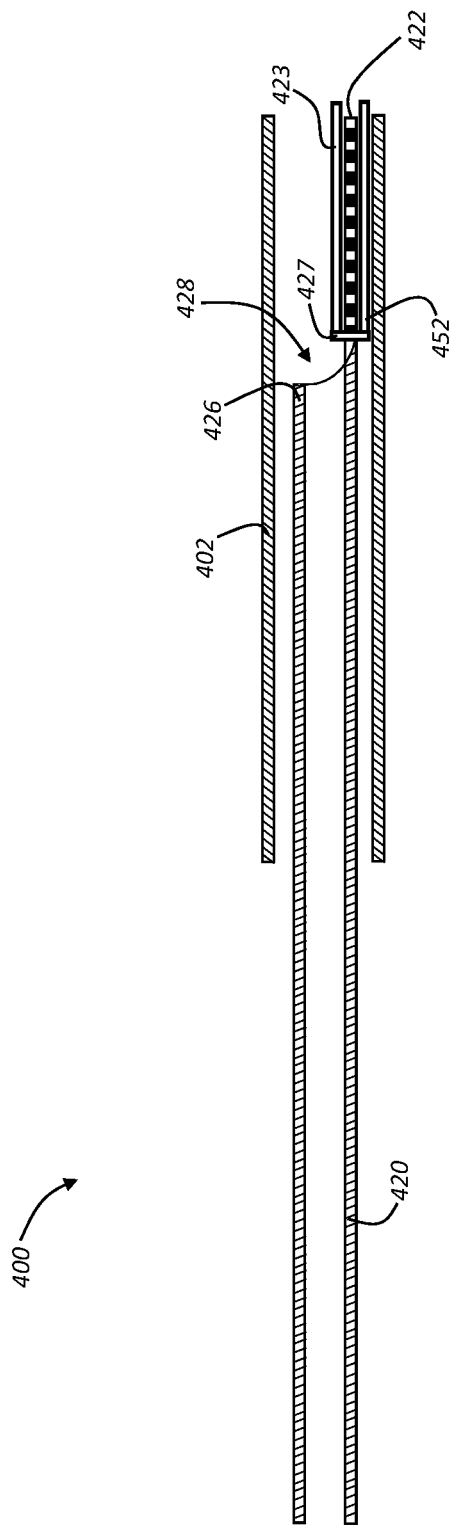
FIG. 4A illustrates a cross-sectional side view of a guide extension catheter, as constructed in accordance with at least one embodiment, partially within a sectioned guide catheter.

FIG. 4A illustrates a cross-sectional side view of a distal portion of a guide extension catheter 400, a portion of which is shown protruding from a guide catheter 402. The guide extension catheter 400 includes an elongate tube member 420 coupled at a proximal end 426 to a push member 422, the push member 422 surrounded by a removable support member 423. The elongate tube member 420 includes a proximal side opening 428, which in this example, features a sloped opening transitioning gradually toward the push member 422. To prevent the removable support member 423 from damaging the proximal end 426 of the elongate tube member 420, a lip member 427 is also included at the distal end 452 of the removable support member 423. The lip member 427 may generally conform to at least a portion of the elongate tube member 420 defining the proximal side opening 428. In some embodiments, the lip member 427 may be shaped to mirror the shape of the proximal side opening 428, for example defining a slanted, sloped or straight surface. As further shown in FIG. 4A, the tube member 420 may have a generally constant diameter in some embodiments. The diameter of the removable support member 423 may vary, provided it is greater than the maximal cross-sectional diameter of the push member 422. In some examples, the cross-sectional diameter of the removable support member 423 may be less than the cross-sectional diameter of the proximal end 426 of the elongate tube member 420, for example ranging from about 0.016 in. to about 0.070 in. or more, or any amount therebetween.

Figure 4B:
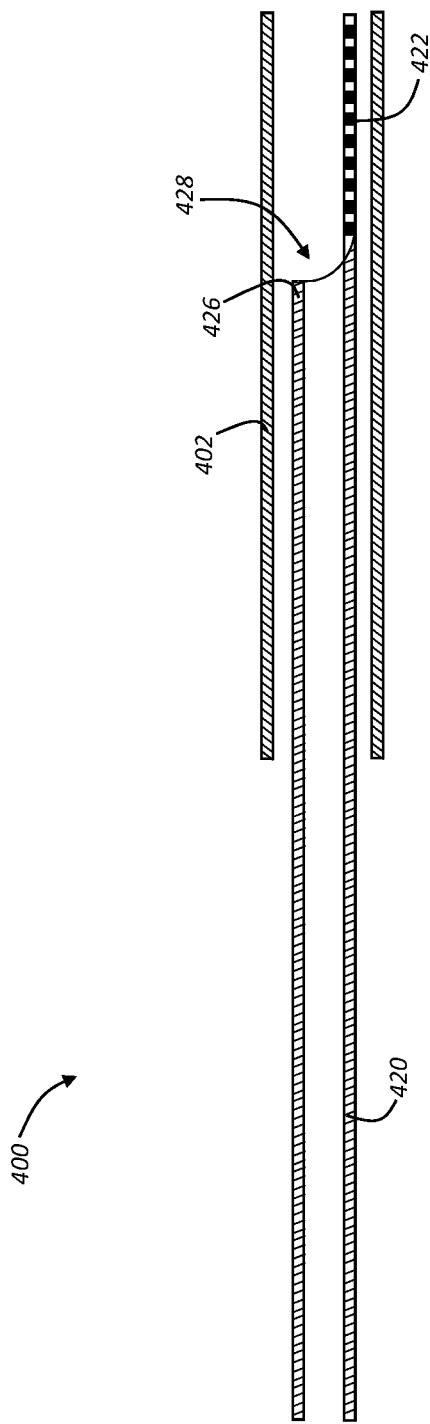
FIG. 4B illustrates a cross-sectional side view of the guide extension catheter of FIG. 4A, after removal of the removable support member.

FIG. 4B illustrates a cross-sectional side view of a distal portion of the guide extension catheter 400 shown in FIG. 4A after removal of the removable support member 423. As shown, the push member 422 remains attached to the proximal end 426 of the elongate tube member 420. The push member 422, alone, may provide sufficient push strength to allow additional advancement of the elongate tube member 420, and may at least provide a level or rigidity and backup support sufficient to maintain the position of the elongate tube member 420 achieved via urging of the removable support member 423.

Figure 5:
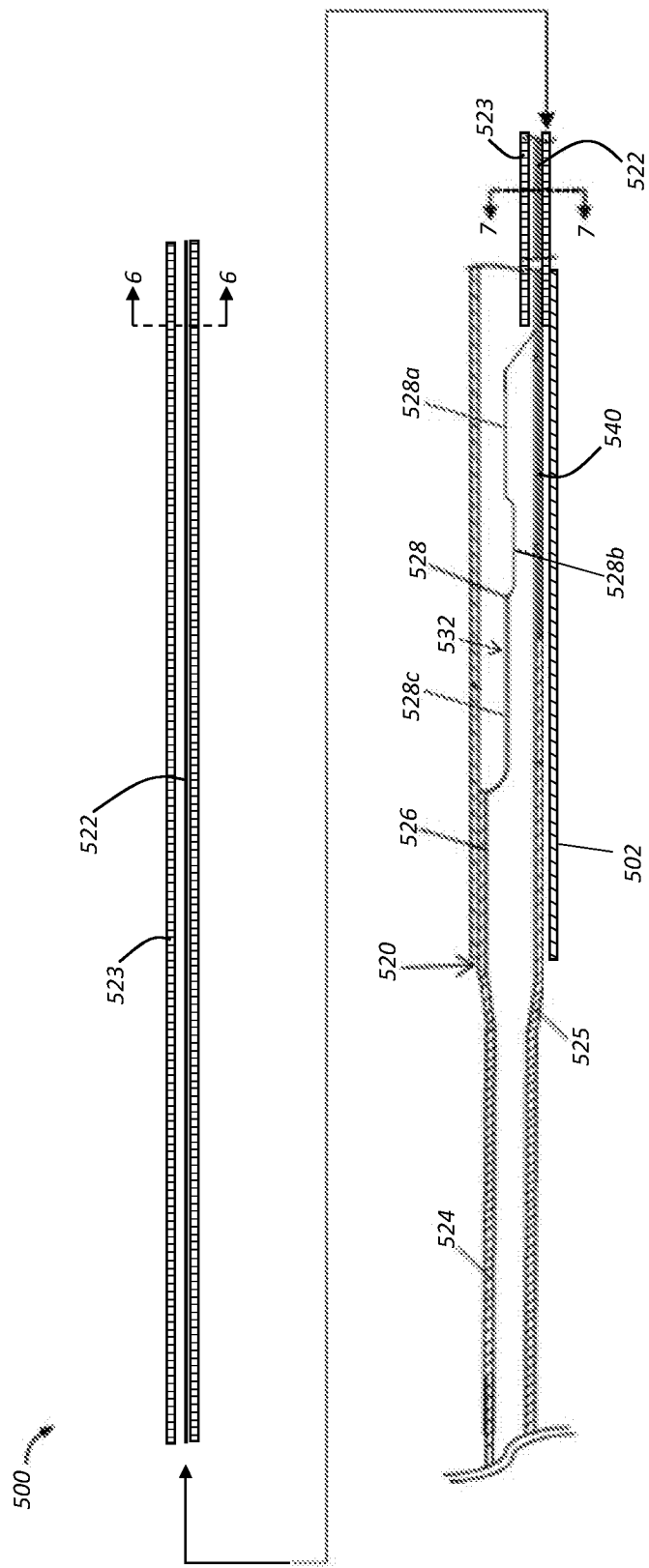
FIG. 5 illustrates a cross-sectional side view of a guide extension catheter, as constructed in accordance with at least one embodiment, partially within a sectioned guide catheter.

FIG. 5 illustrates a cross-sectional side view of an example guide extension catheter 500 partially positioned within a guide catheter 502. This side view illustrates in greater detail the components of the extension catheter 500 according to one embodiment, including a removable support member 523 surrounding at least a portion of a push member 522. The removable support member 523 can be rigid enough to urge the tube member 520 through the vasculature in response to receiving an axial force applied at a proximal end thereof, e.g., by an operating physician. The embodiment shown also illustrates that the tube member 520 may comprise distinct portions having different diameters. As shown, the tube member 520 can define a narrow distal portion 524, a tapered middle portion 525, and a wider proximal portion 526. In additional embodiments, the tube member 520 may not be tapered, and may instead define a constant diameter along its length.

In some embodiments, the push member 522 can be an elongated solid wire of constant or varying dimensions and can be made of a polymeric or metallic material, such as high tensile stainless steel (e.g., 304V, 304L or 316LV), mild steel, nickel-titanium allows, nickel-chromium-molybdenum alloys, nickel-copper alloys, nickel-tungsten alloys or tungsten alloys. The push member 522 can be coated with a hydrophilic, silicone or other friction-reducing material. The stiffness of the push member 522 and/or the removable support member 523 may be uniform, or substantially uniform, along its length, or may define areas having variable stiffness along its length. For example, the push member 522 and/or removable support member 523 may be more flexible near its distal end than its proximal end.

In some examples, the tube member 520 can be formed from an inner polymer layer, an outer polymer layer, and/or a reinforcement member (e.g., braid or coil) disposed between or adjacent to the polymer layers. According to such examples, the inner polymer layer can be composed of, or coated with, silicone, polytetrafluoroethylene (PTFE) or another lubricious material to provide a slippery surface for received interventional devices. The outer polymer layer can include one or more flexible materials, such as polyurethane, polyethylene or polyolefin of sequentially diminishing durometers along the tube member's length, and it can be coated with a friction-reducing material (e.g., a hydrophilic material) to facilitate insertion and trackability through vasculature and a guide catheter. The reinforcing braid or coil, in embodiments featuring a braid or coil, can be formed of stainless steel or a platinum alloy, for example, and can extend between the polymer layers along at least a portion of the tube member's length.

Figure 9A:
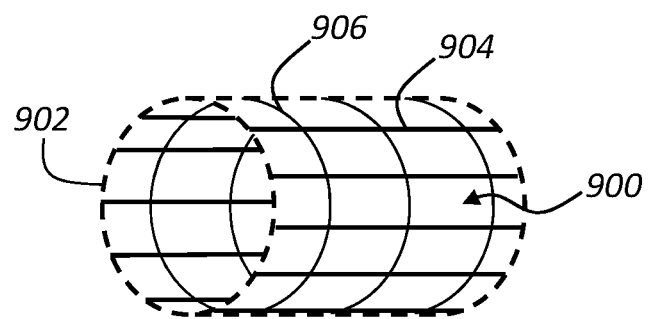
FIG. 9A illustrates a perspective view of a reinforcement member included in a guide extension catheter, as constructed in accordance with at least one embodiment.
Figure 9B:
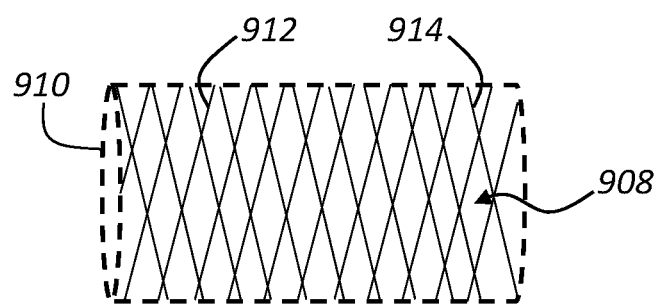
FIG. 9B illustrates a perspective view of another reinforcement member included in a guide extension catheter, as constructed in accordance with at least one embodiment.

The optional reinforcement member disposed between the polymer layers of some elongate tube members 520 can be configured in multiple ways. For instance, the reinforcement member may lack a braid, coil or other distinct reinforcing structure, and may instead comprise one or more materials having greater stiffness than the remaining portions of the tube member 520. In addition or alternatively, embodiments of the reinforcement member can include different reinforcing structures, e.g., a generally rigid sleeve, elongate member, and/or bars or strips of rigid or semi-rigid material, as shown in FIGS. 9A and 9B. Additional components and/or materials configured to increase the rigidity of a portion of the tube member 520 are also contemplated. At least in part because the components of the reinforcement member may vary, methods of assembling the reinforcement member may also vary. For example, if the reinforcement member disposed between the polymer layers of the elongate member 520 includes a coil, various types of coils may be used, and in some examples, each coil can be coupled with other components of the tube member 520 in a distinct manner, which may depend on whether the cross-sectional diameter of the tube member is uniform or varied. In embodiments, if the size of the coil matches the smaller distal portion 524 of the tube member 520, the coil can be first loaded over the distal portion 524. If the size of the coil is larger, such that it approximately matches the larger diameter of the proximal portion 526, the coil can be first loaded onto the proximal portion 526.

The proximal end portion 526 of the tube member 520 can be eccentrically and operably coupled to a distal end portion 540 of the push member 522 at its periphery or circumference and can provide a smooth transition between the members in some examples. The arrangement or configuration of this coupling can vary. In some embodiments, the tube member 520 can include a side opening formed at a proximal end of its peripheral wall. The configuration of the side opening may also vary. For example, the side opening may be approximately perpendicular to the longitudinal axis of the push member 522, or the side opening may be sloped or slanted such that the transition between the push member 522 and the full circumferential portion of the tube member 520 is relatively gradual. In some examples, the push member 522 can be disposed within the opening. Inserting the push member 522 into the opening can result in a mechanical coupling between the members and additional or alternative bonds (e.g., adhesive bonds, thermal bonds, welds, brazes, etc.) can be utilized. The distal end portion 540 of the push member 522 can be flattened in some embodiments to provide a larger surface area to secure to the tube member 520. In addition or alternatively, coupling mechanisms facilitated by a separate component 532 (e.g., a metal or polymer skived (slanted) collar or concave track) bonded between or integrated with the proximal end portion 526 of the tube member 520 or the distal end portion 540 of the push member 522 are also contemplated. Metallic or polymeric structures forming the separate component 532 can become less stiff and more flexible in a proximal-to-distal direction, for instance, to provide a gradual flexibility transition between the more rigid push member 522 and the more flexible tube member 520.

In embodiments featuring a concave track 528, such as the example shown in FIG. 5, the degree of enclosure defined by the concave track 528 can vary along its length. In various examples, a first segment 528*a* of the concave track 528 can define an enclosure ranging from less than about 140°, about 140° to about 260° or greater, about 160° to about 240°, about 180° to about 220°, about 190° to about 210°, about 195° to about 205°, or any degree therebetween. A second segment 528*b* of the concave track can define an enclosure ranging from less than 110°, about 110° to about 230° or greater, about 130° to about 210°, about 150° to about 190°, about 160° to about 180°, or about 165° to about 175°, or any degree therebetween. A third segment 528*c*, closer to the tube member 520, can define an enclosure ranging from less than about 140°, to about 140° to about 260° or greater, about 160° to about 240°, about 180° to about 220°, about 190° to about 210°, about 195° to about 205°, or any degree therebetween. The third segment 528*c* may transition to 360° just before reaching the most proximal end of the tube member's proximal portion 526. In one embodiment, the first segment 528*a* of the concave track 528 can define an approximately 200° enclosure, the second segment 528*b* of the concave track can define an approximately 170° enclosure, and the third segment 528*c*, closer to the tube member 520, can define an approximately 200° enclosure, which transitions to 360° just before reaching the most proximal end of the tube member's proximal portion 526. Accordingly, the concave track 528 may transition, proximally to distally, from more enclosed to less enclosed, and back to more enclosed before reaching the proximal end portion 526 of the tube member 520. The specific degree of enclosure defined by each portion of the concave track 528 may vary, along with the number of distinct portions constituting the concave track 528. For example, the degree of enclosure defined by each portion may be increased or decreased by up to 5°, 10°, 15°, 20°, 25°, 30°, 40°, 50°, 60°, or more. In operation, the intermediary valley of the concave track 528, i.e., the second segment 528*b*, along with the embedded push member 522, may be urged to one side of the guide catheter's inner wall surface such that the track 528 and push member 522 may be concentrically aligned within guide catheter 502, thereby providing a clear path through the guide catheter and into the tube member 520 for a guidewire and a treating catheter. This clear path can eliminate twisting and prevent a guidewire, e.g., guidewire 212, from becoming entangled with, e.g., wrapped around, the push member 522 during use of the guide extension catheter 500. Alleviation of twisting may be especially apparent in operations requiring multiple, simultaneously inserted guidewires.

In some embodiments, the concave track 528 can define a partially cylindrical opening, e.g., resembling a half-pipe, and having a length of about 1 cm to about 4 cm, 8 cm, 12 cm, 16 cm, 18 cm, 20 cm, 22 cm, 24 cm, 26 cm, or more, or any length therebetween. In one example, the concave track 528 may be about 17 cm long. In various embodiments, the length of each discernible portion 528*a*, 528*b*, 528*c* of the concave track 528 may range from about 1 cm, 2 cm, 4 cm, 6 cm, 8 cm, 10 cm, or 12 cm. The length of each portion 528*a*, 528*b*, 528*c* may be the same or different. In some examples, the concave track 528 may include less than three distinct portions. For example, the concave track 528 may define an elongated tapered portion. The concave track 528 can be accessible from a longitudinal side defined transverse to a longitudinal axis of the tube member 520 and can provide a larger area to receive an interventional device into the tube member than an area associated with an opening oriented perpendicular to the longitudinal axis of the tube member 520. Optionally, the concave track 528 can be sized larger than the proximal end portion 526 of the tube member 520 to more effectively align and funnel a treating catheter across the coupling transition and into the tube member 520. This larger size of the concave track 528 can be accomplished by incorporating a nickel-titanium alloy, for example, which can expand post-implant to a size of the guide catheter's inner wall surface.

Markers on the push member 522, the tube member 520, and/or the removable support member 523 can allow an operating physician to identify positioning of the guide extension catheter's components relative to patient anatomy, the guide catheter 502, and any interventional devices used during a procedure. For example, one or more depth markers can be printed on an outer surface of the push member 522 and/or the removable support member 523 and can be positioned at predetermined lengths relative to a distal end of the tube member 520. One or more radiopaque marker bands can be positioned on the tube member 520. The marker bands can be composed of tungsten, platinum or an alloy thereof and can have a metallic band structure. Alternatively, for space conservation reasons, the marker bands can be formed by impregnating portions of the tube member 520 with a radiopaque filler material, such as barium sulfate, bismuth trioxide, bismuth carbonate, powdered tungsten, powdered tantalum or the like. A first marker band can be positioned slightly distal to a fully-round entrance of the tube member 520 and a second marker band can be positioned near the tube member's distal end, for example.

Methods of manufacturing the guide extension catheters described herein may involve stretching an inner PTFE lining of the elongate tube member 520. In embodiments featuring a tapered elongate tube member 520, the PTFE lining may require excess stretching relative to comparable, but non-tapered tube members, and the outer surface of the lining can be etched to maintain the desired polymer chemistry of the PTFE, thereby ensuring adhesion between the fluoropolymers of the lining and an outer polymer layer (e.g., PEBAX) wrapping.

Figure 6:
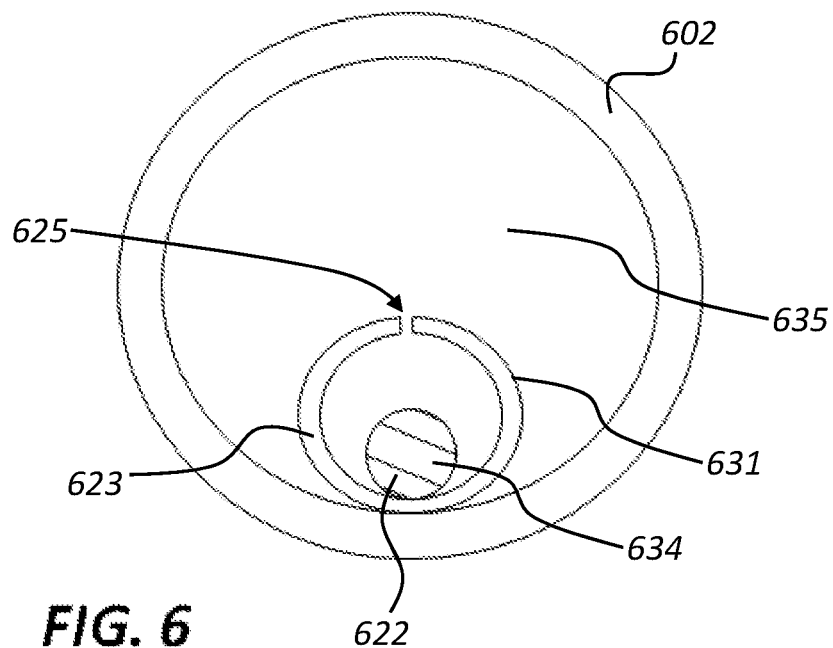
FIGS. 6-7 illustrate cross-sectional views along the length of a guide extension catheter, as constructed in accordance with at least one embodiment, within a guide catheter.

FIG. 6 illustrates a cross-sectional view of a proximal end portion 634 of an example push member 622, such as along line 6-6 of FIG. 5, within a guide catheter 602. The push member 622 defines a circular cross-section in the example shown, but the cross-sectional shape and dimensions of the push member 622 may vary. For example, the push member 622 can comprise an arcuate or flat, sheet-like cross-sectional shape, and rectangular, irregular, oval, oblong cross-sectional shapes are also within the scope of this disclosure. A proximal end portion 631 of a removable support member 623 is also shown, the support member 623 surrounding the push member 622. The removable support member 623 can include a stainless steel hypotube in some examples, or a tubular structure comprised of various materials in additional embodiments. To facilitate its removal after insertion, the removable support member 623 can further define a narrow slit 625. The width and position of the slit 625 may vary. For example, the width of the slit 625 in its unbiased configuration may be about 5%, 10%, 20%, 30%, 40%, 50% or more of the width of the push member 622. In specific embodiments, the unbiased slit 625 may range from less than or equal to about 0.005 in. to about 0.012 in or more, or any width therebetween.

Due to the combined structural support of the removable support member 623 and the narrow cross-section of the push member 622, the two components can together comprise sufficient axial or column strength for force transfer from an operating physician to the rest of the guide extension catheter without reducing the effective delivery area 635 within the guide catheter 602 through which an interventional device can be advanced.

Figure 7:
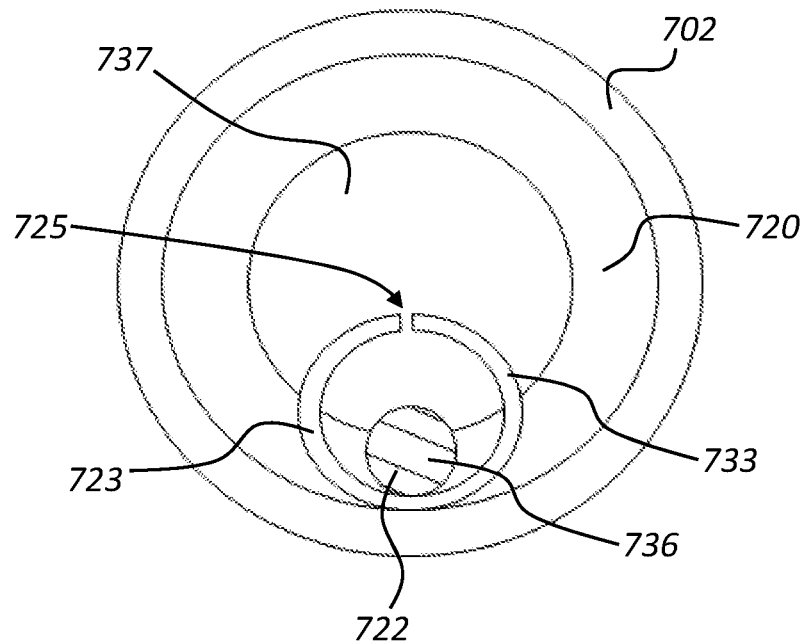

FIG. 7 illustrates a cross-sectional view of a distal end portion 736 of an example push member 722, such as along line 7-7 of FIG. 5, within a guide catheter 702. The distal end portion 736 can be substantially circular in cross-section. The distal end portion 736 can be coupled to a tube member 720. Additional cross-sectional shapes and dimensions of the distal end portion 736 are also contemplated, and the guide extension catheters disclosed herein are not limited to one or more configurations of the push member 722. A distal end portion 733 of the removable support member 723 is also shown. The distal end portion 733, upon receiving an axial or longitudinal force by an operating physician, may contact and push the tube member 720. The cross-sectional diameter of the removable support member 723 may vary, and may be greater than the cross-sectional diameter of the push member 722 but less than or equal to the cross-sectional diameter of the tube member 720.

FIGS. 6 and 7 illustrate that the push member 622, 722 of a guide extension catheter can be designed to be sufficiently small taking up relatively little space within the lumen of a guide catheter, and in tandem with the removable support member 623, 723, can also provide enhanced pushability and kink resistance when advancing the guide extension catheter during an interventional procedure. Accordingly, use of the present guide extension catheters allows for an interventional device to be advanced through and beyond the guide catheter to reach a desired distal target location for intervention.

Figure 8:
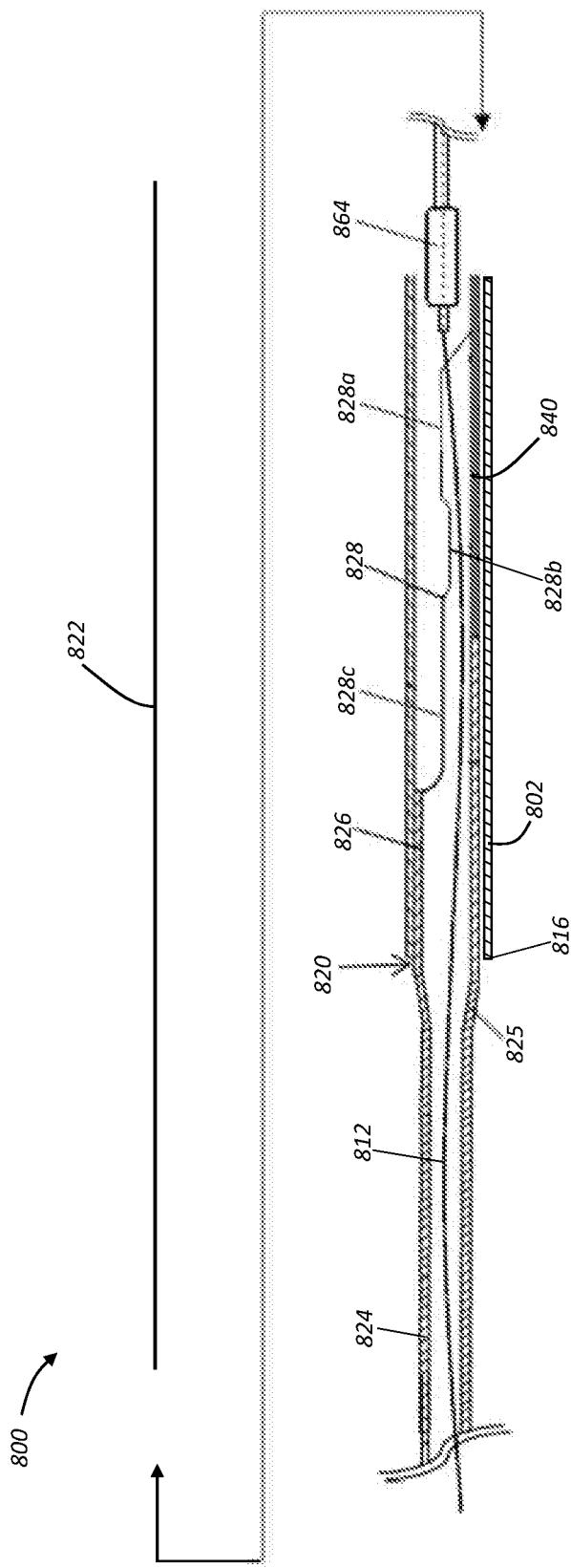
FIG. 8 illustrates a cross-sectional side view of a guide extension catheter, as constructed in accordance with at least one embodiment and after removal of the removable support member, and an interventional device partially within a sectioned guide catheter.

FIG. 8 illustrates a side view of an example guide extension catheter 800 positioned within a guide catheter 802 and used in conjunction with a guidewire 812 and a treating catheter 864. With the guidewire 812 and the guide catheter 802 positioned as desired, a tube member 820 of the guide extension catheter 800 can be backloaded from its narrow distal end portion 824 onto a proximal end of the guidewire 812 and advanced through a hemostasis valve coupled to the guide catheter 802. As shown, the tube member 820 of the guide extension catheter 800 can be advanced beyond a distal end 816 of the guide catheter 802 under fluoroscopy. When so arranged, portions of the tube member 820 can engage an ostium and extend within a portion of a coronary artery to help maintain the position of the guide catheter 802 as the treating catheter 864 is advanced. As further shown, embodiments of the guide extension catheter 800 can include a concave track 828, which may provide a variable degree of enclosure at portions 828a, 828b, and 828c to prevent or reduce twisting of the guidewire 812.

FIG. 9A illustrates an example reinforcement member 900, which may be included in some embodiments to increase the stiffness of the elongate tube member 902 of a guide extension catheter (only a portion of which is shown). As described above, the reinforcement member 900 may be sandwiched between two polymer layers constituting the elongate tube member 902. The reinforcement member 900 can include a plurality of longitudinal bars or strips 904, which may be interlaced with one or more cross-bars or strips 906. The strips 904, 906 may be arranged perpendicularly, or substantially perpendicularly, with respect to each other, or they may be diagonally arranged. In some examples, only the longitudinal or the cross strips may be included. The reinforcement member 900 can extend around the entire perimeter of the elongate tube member 902, or only a portion thereof.

FIG. 9B illustrates another example reinforcement member 908 included with an elongate tube member 910 (only a portion of which is shown). In this example, the reinforcement member 908 can be comprised of spiraling bars or strips 912, 914, which may criss-cross. In embodiments, strips in only one spiral direction, i.e., 912 or 914, may be included. Any suitable angle or combination of angles of the spiral with respect to the longitudinal axis of the tube may be used. Like reinforcement member 900, reinforcement member 908 can be sandwiched between individual layers constituting the elongate tube member 910. The particular configuration of the reinforcement member, its location and/or length may vary in different embodiments of the guide extension catheters disclosed herein, which are not confined to examples including reinforcement members, or specific embodiments thereof. The materials constituting the reinforcement member may also vary. In examples, the reinforcement member can include stainless steel, a platinum alloy, and/or one or more polymers, for instance.

EXAMPLES

The above Detailed Description is intended to be illustrative and not restrictive. The above-described embodiments, or one or more features or components thereof, can be used in varying combinations with each other unless clearly stated to the contrary. Other embodiments or features or components thereof can be used, such as by one of ordinary skill in the art upon reviewing the above Detailed Description. Also, various features or components have been grouped together to streamline the disclosure. This should not be interpreted as intending that an unclaimed disclosed feature or component is essential to any claim. Rather, inventive subject matter can lie in less than all features of a particular disclosed embodiment. Thus, the following claim examples are hereby incorporated into the Detailed Description, with each example standing on its own as a separate embodiment.

In Example 1, a guide extension catheter for use with a guide catheter can comprise an elongate tube member, a push member, and a removable support member. The elongate tube member has a cross-sectional outer diameter sized to be insertable through a cross-sectional inner diameter of the guide catheter and has a cross-sectional inner diameter defining a coaxial lumen through which an interventional cardiology device is insertable. The push member is proximal of and operably connected to the elongate tube member and can have a maximal cross-sectional dimension that is smaller than the cross-sectional outer diameter of the elongate tube member. A collective length of the elongate tube member and the push member is longer than the guide catheter, such that when at least a distal portion of the elongate tube member is extended distally of a distal end of the guide catheter, at least a portion of the proximal portion of the push member extends proximally through a hemostatic valve in common with the interventional cardiology device. The removable support member surrounds at least a portion of the push member and can have a structure that, when surrounding the push member, is more rigid along its longitudinal axis than the elongate tube member.

In Example 2, the guide extension catheter of Example 1 can optionally be configured such that the removable support member includes a hypotube having a cross-sectional dimension that is greater than the maximal cross-sectional dimension of the push member.

In Example 3, the guide extension catheter of any one of Examples 1 or 2 can optionally be configured such that the removable support member includes a longitudinal slit along a length thereof.

In Example 4, the guide extension catheter of any one or any combination of Examples 1-3 can optionally be configured such that the removable support member comprises a stop member at a distal end thereof. The stop member can comprise a resilient lip configured to prevent damage to the elongate tube member.

In Example 5, the guide extension catheter of any one or any combination of Examples 1-4 can optionally be configured such that the push member comprises a rod or wire.

In Example 6, the guide extension catheter of Example 5 can optionally be configured such that the maximal cross-sectional dimension of the push member is between about 0.006 inches and about 0.016 inches, inclusive.

In Example 7, the guide extension catheter of any one or any combination of Examples 1-6 can optionally be configured such that a distal portion of the elongate tube member comprises a hydrophilic coating and a proximal portion of the elongate tube member does not comprise a hydrophilic coating.

In Example 8, the guide extension catheter of Example 7 can optionally be configured such that the distal portion comprises a length of about 5 cm to about 20 cm, inclusive, extending proximally from a distal tip of the elongate tube member.

In Example 9, the guide extension catheter of any one or any combination of Examples 1-8 can optionally be configured such that the elongate tube member includes a flexible cylindrical distal tip portion and a flexible cylindrical portion with a reinforcement member that is proximal to the flexible cylindrical distal tip portion. A distal portion of the elongate tube member can be more flexible than a proximal portion of the elongate tube member.

In Example 10, the guide extension catheter of any one or any combination of Examples 1-9 can optionally further comprise structure defining a proximal side opening extending for a distance along the longitudinal axis, and accessible from a longitudinal side defined transverse to the longitudinal axis, to receive the interventional cardiology device into the coaxial lumen while a proximal portion of the elongate tube member remains within the lumen of the guide catheter.

In Example 11, the guide extension catheter of Example 10 can optionally be configured such that the proximal side opening defines a concave track configured to guide the interventional cardiology device into the coaxial lumen of the elongate tube member.

In Example 12, the guide extension catheter of any one of Examples 10 or 11 can optionally be configured such that the structure includes a component bonded between a distal portion of the push member and the proximal portion of the elongate tube member.

In Example 13, the guide extension catheter of any one of Examples 10 or 11 can optionally be configured such that the structure includes a component integrated with a distal portion of the push member or the proximal portion of the elongate tube member.

In Example 14, the guide extension catheter of any one or any combination of Examples 1-13 can optionally be configured such that the interventional cardiology device is a stent, a stent catheter, or a balloon catheter.

In Example 15, a method can comprise advancing a distal end of a guide catheter having a continuous lumen through a blood vessel to an ostium of a coronary artery; and advancing a distal end of a guide extension catheter through, and beyond the distal end of, the guide catheter, including advancing a push member of the guide extension catheter that is at least partially surrounded by a removable support member into the continuous lumen of the guide catheter. The push member is proximal of and operably connected to an elongate tube member of the guide extension catheter and can have a maximal cross-sectional dimension at a proximal portion that is smaller than a cross-sectional outer diameter of the elongate tube member. The push member has a length such that, when combined with a length of the elongate tube member, a distal end portion of the elongate tube member is extendable through the continuous lumen of the guide catheter and beyond the distal end of the guide catheter while a proximal end of the push member is extendable through a hemostatic valve positioned at a proximal end of the guide catheter. The removable support member can comprise a structure more rigid along its longitudinal axis than the elongate tube member and can have a cross-sectional dimension that is greater than the maximal cross-sectional dimension of the push member.

In Example 16, the method of Example 15 can optionally be configured such that advancing the push member that is at least partially surrounded by the removable support member into the continuous lumen of the guide catheter includes advancing a push member that is at least partially surrounded by a hypotube into the continuous lumen of the guide catheter.

In Example 17, the method of Example 16 can optionally be configured such that the hypotube includes a longitudinal slit along a length thereof. The longitudinal slit can be biased toward a closed position.

In Example 18, the method of Example 17 can optionally further comprise urging the push member through the longitudinal slit and removing the removable support member from the guide catheter.

In Example 19, the method of any one or any combination of Examples 15-18 can optionally be configured such that advancing the push member that is at least partially surrounded by the removable support member into the continuous lumen of the guide catheter includes urging a stop member, located at a distal end of the removable support member, against a proximal end of the elongate tube member.

In Example 20, the method of any one or any combination of Examples 15-19 can optionally be configured such that advancing the push member that is at least partially surrounded by the removable support member into the continuous lumen of the guide catheter includes advancing a rod or wire that is at least partially surrounded by a removable support member into the continuous lumen of the guide catheter.

In Example 21, the method of any one or any combination of Examples 15-20 can optionally be configured such that advancing the distal end of the guide extension catheter through, and beyond the distal end of, the guide catheter includes leveraging lubricity afforded by a hydrophilic coating on the distal 5 cm to 20 cm of the elongate tube member.

Closing Notes

The above Detailed Description includes references to the accompanying drawings, which form a part of the Detailed Description. The Detailed Description should be read with reference to the drawings. The drawings show, by way of illustration, but not by way of limitation, specific embodiments in which the present guide extension catheters and related methods can be practiced. These embodiments are also referred to herein as "examples."

Certain terms are used throughout this patent document to refer to particular features or components. As one skilled in the art will appreciate, different people may refer to the same feature or component by different names This patent document does not intend to distinguish between components or features that differ in name but not in function. For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (i.e., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating caregiver. "Distal" and "distally" refer to a position that is distant from, or in a direction away from, the caregiver. "Proximal" and "proximally" refer to a position that is near, or in a direction toward, the caregiver. And the term "interventional device (s)" is used to include, but is not limited to, guidewires, balloon catheters, stents and stent catheters.

The scope of the present guide extension catheters and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the present patent matter's technical disclosure. It is submitted with the understanding that it will not be used to interpret or limit the scope or meaning of any claim.

What is claimed is:

1. A guide extension catheter for use with a guide catheter, the guide extension catheter comprising:
    an elongate tube member having a cross-sectional outer diameter sized to be insertable through a cross-sectional inner diameter of the guide catheter and having a cross-sectional inner diameter defining a coaxial lumen through which an interventional cardiology device is insertable;
    a push member that is proximal of and operably connected to the elongate tube member, the push member having a maximal cross-sectional dimension that is smaller than the cross-sectional outer diameter of the elongate tube member and having a length that when combined with a length of the elongate tube member forms a collective length that is longer than the guide catheter, such that when at least a distal portion of the elongate tube member extends distally of a distal end of the guide catheter, at least a portion of the push member extends proximally of a proximal end of the guide catheter; and
    a removable support member surrounding at least a portion of the push member, the removable support member comprising a structure that, when surrounding the push member, is more rigid along a longitudinal axis of the structure than the elongate tube member, wherein the removable support member comprises a stop member at a distal end thereof, the stop member comprising a resilient lip configured to prevent damage to the elongate tube member.

2. The guide extension catheter of claim 1, wherein the removable support member includes a hypotube having a cross-sectional dimension that is greater than the maximal cross-sectional dimension of the push member.

3. The guide extension catheter of claim 1, wherein the removable support member includes a longitudinal slit along a length thereof.

4. The guide extension catheter of claim 1, wherein the push member comprises a rod or a wire.

5. The guide extension catheter of claim 1, wherein the maximal cross-sectional dimension of the push member is between about 0.006 inches and about 0.016 inches, inclusive.

6. The guide extension catheter of claim 1, wherein the distal portion of the elongate tube member comprises a hydrophilic coating and a proximal portion of the elongate tube member does not comprise a hydrophilic coating.

7. The guide extension catheter of claim 6, wherein the distal portion of the elongate tube member comprises a length of about 5 cm to about 20 cm, inclusive, extending proximally from a distal tip of the elongate tube member.

8. The guide extension catheter of claim 1, wherein the elongate tube member includes a flexible cylindrical distal tip portion and a flexible cylindrical portion with a reinforcement member that is proximal to the flexible cylindrical distal tip portion, and wherein the distal portion of the elongate tube member is more flexible than a proximal portion of the elongate tube member.

9. A guide extension catheter for use with a guide catheter, the guide extension catheter comprising:
an elongate tube member having a cross-sectional outer diameter sized to be insertable through a cross-sectional inner diameter of the guide catheter and having a cross-sectional inner diameter defining a coaxial lumen through which an interventional cardiology device is insertable, the elongate tube member including a proximal side opening accessible from a longitudinal side defined transverse to a longitudinal axis of the elongate tube member to receive the interventional cardiology device into the coaxial lumen while a proximal portion of the elongate tube member remains within a lumen of the guide catheter;
a push member that is proximal of and operably connected to the elongate tube member, the push member having a maximal cross-sectional dimension that is smaller than the cross-sectional outer diameter of the elongate tube member and having a length that when combined with a length of the elongate tube member forms a collective length that is longer than the guide catheter, such that when at least a distal portion of the elongate tube member extends distally of a distal end of the guide catheter, at least a portion of the push member extends proximally of a proximal end of the guide catheter; and
a removable support member surrounding at least a portion of the push member, the removable support member comprising a structure that, when surrounding the push member, is more rigid along a longitudinal axis of the structure than the elongate tube member.

10. The guide extension catheter of claim 9, wherein the proximal side opening defines a concave track configured to guide the interventional cardiology device into the coaxial lumen of the elongate tube member.

11. The guide extension catheter of claim 9, wherein the proximal side opening includes a component bonded between a distal portion of the push member and the proximal portion of the elongate tube member.

12. The guide extension catheter of claim 11, wherein the component is integrated with a distal portion of the push member or the proximal portion of the elongate tube member.

13. The guide extension catheter of claim 9, wherein a distal end of the distal portion of the elongate tube member comprises a hydrophilic coating and the proximal portion of the elongate tube member does not comprise a hydrophilic coating.

14. The guide extension catheter of claim 9, wherein the elongate tube member includes a flexible cylindrical distal tip portion and a flexible cylindrical portion with a reinforcement member that is proximal to the flexible cylindrical distal tip portion, and wherein the distal portion of the elongate tube member is more flexible than the proximal portion of the elongate tube member.

15. A method, comprising:
advancing a distal end of a guide catheter having a continuous lumen through a blood vessel to an ostium of a coronary artery; and
advancing a distal end of a guide extension catheter through, and beyond the distal end of, the guide catheter, including advancing a push member of the guide extension catheter that is at least partially surrounded by a removable support member into the continuous lumen of the guide catheter and urging a stop member, located at a distal end of the removable support member and comprising a resilient lip configured to prevent damage to the elongate tube member, against a proximal end of the elongate tube member,
the push member proximal of and operably connected to an elongate tube member of the guide extension catheter and having a maximal cross-sectional dimension at a proximal portion that is smaller than a cross-sectional outer diameter of the elongate tube member, the push member having a length such that, when combined with a length of the elongate tube member, a distal end portion of the elongate tube member is extendable through the continuous lumen of the guide catheter and beyond the distal end of the guide catheter while a proximal end of the push member is extendable through a hemostatic valve positioned at a proximal end of the guide catheter, and
the removable support member comprising a structure more rigid along a longitudinal axis of the removable support member than a rigidity of the elongate tube member along a longitudinal axis of the elongate tube member, the removable support member having a cross-sectional dimension that is greater than the maximal cross-sectional dimension of the push member.

16. The method of claim 15, wherein advancing the push member that is at least partially surrounded by the removable support member into the continuous lumen of the guide catheter includes advancing the push member that is at least partially surrounded by a hypotube into the continuous lumen of the guide catheter.

17. The method of claim 16, wherein the hypotube includes a longitudinal slit along a length thereof, the longitudinal slit biased toward a closed position.

18. The method of claim 17, further comprising urging the push member through the longitudinal slit and removing the removable support member from the guide catheter.

19. The method of claim 15, wherein advancing the push member that is at least partially surrounded by the removable support member into the continuous lumen of the guide catheter includes advancing a rod or a wire that is at least partially surrounded by the removable support member into the continuous lumen of the guide catheter.

20. The method of claim 15, wherein advancing the distal end of the guide extension catheter through, and beyond the distal end of, the guide catheter includes leveraging lubricity afforded by a hydrophilic coating on a distal 5 cm to 20 cm of the elongate tube member.

* * * * *